US012770304B2

(12) United States Patent
Ahmed

(10) Patent No.: US 12,770,304 B2
(45) Date of Patent: Oct. 20, 2026

(54) ELECTRONIC EVALUATION SYSTEM

(71) Applicant: Leeza Ahmed, Chantilly, VA (US)

(72) Inventor: Leeza Ahmed, Chantilly, VA (US)

(*) Notice: Subject to any disclaimer, the term of this patent is extended or adjusted under 35 U.S.C. 154(b) by 60 days.

(21) Appl. No.: 17/872,092

(22) Filed: Jul. 25, 2022

(65) Prior Publication Data

US 2024/0029862 A1 Jan. 25, 2024

(51) Int. Cl.
*G06T 11/60* (2026.01)
*G06T 13/80* (2011.01)
*G16H 20/70* (2018.01)

(52) U.S. Cl.
CPC .............. *G06T 11/60* (2013.01); *G06T 13/80* (2013.01); *G16H 20/70* (2018.01)

(58) Field of Classification Search
CPC ........ G16H 20/70; G16H 80/00; G06T 11/60; G06T 13/80; G06T 13/08
See application file for complete search history.

(56) References Cited

U.S. PATENT DOCUMENTS

2015/0379055 A1* 12/2015 Jeong .................. G06F 3/04817 707/741
2016/0077547 A1* 3/2016 Aimone ................ A61B 5/1114 345/8
2018/0261332 A1* 9/2018 Baeuerle ................ G16H 70/60
2019/0094981 A1* 3/2019 Bradski ................ G06V 40/168
2019/0189259 A1* 6/2019 Clark ...................... G16H 10/60
2024/0028106 A1* 1/2024 Elor ....................... G06T 19/006
2024/0070251 A1* 2/2024 Maizels .................. G10L 13/02

OTHER PUBLICATIONS

Morales-Rodriguez et al., "Design of an emotional and social interaction paradigm for the animation of 3D characters: the case of a therapy for brain injured people (the mirror neuron paradigm)," Virtual Reality, 11:175-184, Feb. 2006 (Year: 2006).*

Fabri et al., "Emotionally Expressive Avatars for Chatting, Learning and Therapeutic Intervention," 12th International Conference, HCI International 2007, Beijing, China, 275-285, Jul. 22-27, 2007 (Year: 2007).*

* cited by examiner

*Primary Examiner* — Shahid Merchant
*Assistant Examiner* — Benjamin L. Hanks

(57) ABSTRACT

A device includes memory and a processor. The device receives a request to generate an electronic character. The device then receives an electronic communication that includes information about different features of the electronic character. The device then generates an electronic character that includes the different features. The device then generates display an electronic light being. The device then generates generate an action by the electronic light being. The device then generates generate the same action by the electronic character.

8 Claims, 15 Drawing Sheets

ELECTRONIC EVALUATION SYSTEM

BACKGROUND

Individuals may have mental health issues that may require a person to seek the assistance of a therapist or other type of mental health professional. While these resources can be invaluable in assisting with various mental health issues, there is no current way to provide a low-cost and accessible resource that allows individuals to cope with their mental health issues until they are available to see a mental health professional.

BRIEF DESCRIPTION OF DRAWINGS

FIGS. 1A-1D are diagrams of an example environment in which systems and/or methods described herein may be implemented;

DETAILED DESCRIPTION OF PREFERRED EMBODIMENTS

Figure 1A:
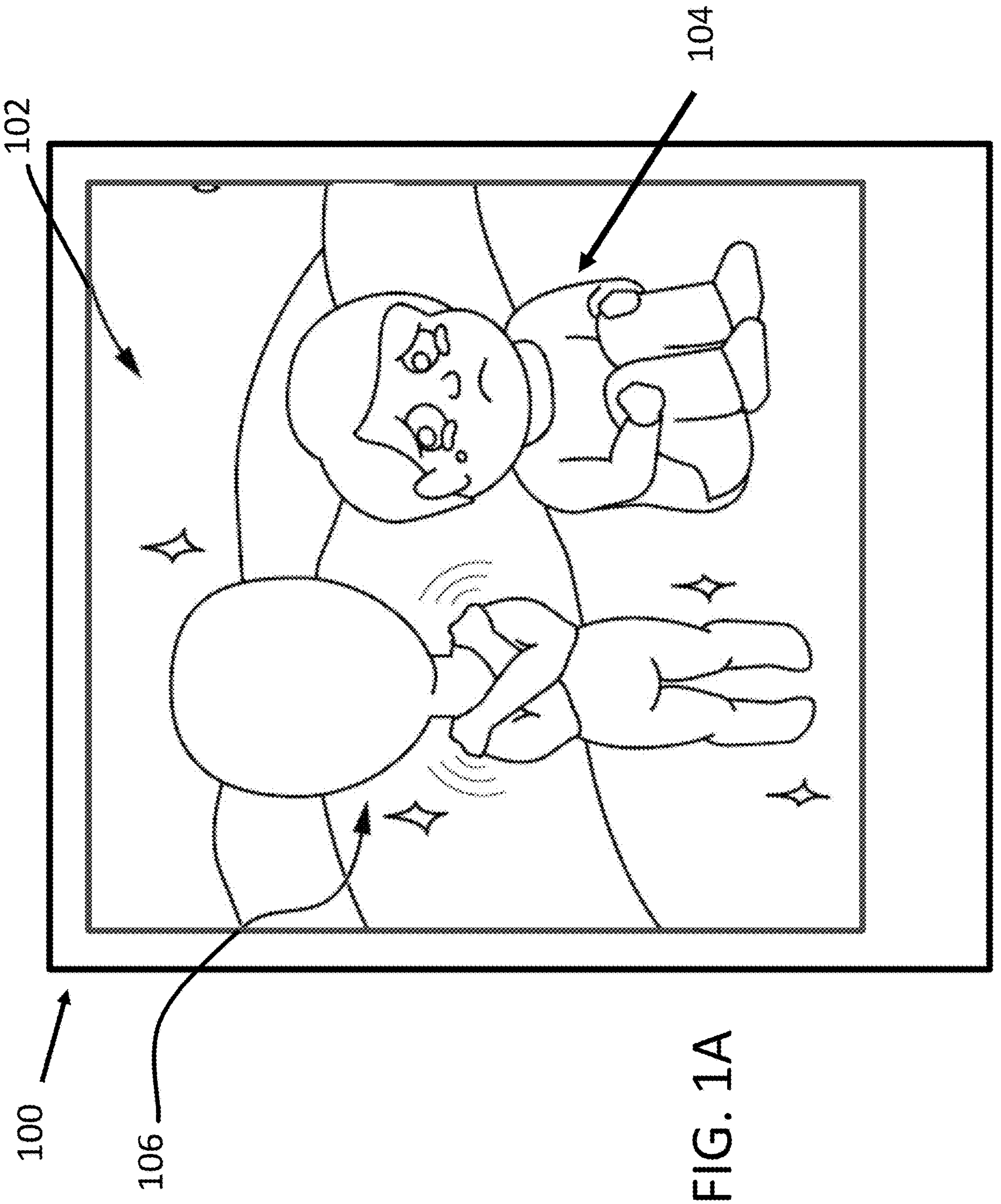

The following detailed description refers to the accompanying drawings. The same reference numbers in different drawings may identify the same or similar elements.

Systems, devices, and/or methods described herein may allow for a user, using an electronic application implemented on a computing device (e.g., smartphone, laptop, etc.), to verify provide a user with intermediary electronic communications during a period of time when the user is having a mental health issue and requires an electronic communication with a mental health professional. In providing these intermediary electronic communications, the user may reduce the need to initiate multiple electronic communications with a mental health professional as the user has become emotionally calmed down due to the intermediary electronic communications.

In embodiments, to receive intermediary electronic communications, a user may input electronic application (to be described further) personal information. Based on the personal information, the electronic application may generate one or more icons and/or other types of symbols that may be used with various other electronic communications that are used by the user to provide a temporary relief. In embodiments, the electronic communications generated by the user may provide the user with information on how to use icons, symbols, avatars, and other features to assist the user on how to electronically communicate with the electronic application. Based on the temporary relief, the user does not need to immediately send electronic communications to a mental health professional until at a later time.

In embodiment, the electronic application may generate electronic instructions that will include an electronic image of a blank character model. In embodiments, the electronic application may receive electronic communications that customize the blank character model to include additional electronic features, such as hair color, hair texture, hair style, skin color, skin texture, nose shape, stomach size, stomach rolls, discoloration, cellulite, arms or no arms, legs or no legs, arm shape, leg shape, eye shape, eye color, eyelash length, freckles, moles, eyebrow shape, eyebrow color, lip shape, lip color, clothes, head coverings, and/or any other features.

In embodiments, once the electronic character model has had all features filled in, the electronic application may place the character within a background screen that may include multiple icons. In embodiments, the icons may include different features, such as, but not limited to, a pie chart, a small heart, and a small white or red cross.

In embodiments, selecting one of the icons may generate additional icons associated with different electronic information displayed by the electronic application. In embodiments, the additional electronic information may be associated with different types of emotions: sad, disgusted, angry, fearful, bad, surprised, and happy. In embodiments, once the use selects one of the icons, further electronic information associated with that emotion. For example, if the user selects the sad emotion, an electronic icon may display additional information associated with hurt, depressed, guilty, despair, vulnerable, and lonely.

In embodiments, the electronic application may generate an electronic communication that requests if the user would like any other words that describe the user's emotional state. In embodiments, after the user has chosen the word to describe their emotional state, the electronic application begins an electronic communication process (such as an electronic coping mechanism lesson).

In embodiments, the electronic character changes its electronic features based on the word (or words) that were chosen by the user. In embodiments, the electronic application will emote the chosen word and also generate another character with a very pale yellow to white light will appear next to the user's generated electronic character. In embodiments, this character, known as the light being, may generate electronic communications with the electronically generated character. In embodiments, the light being may have the outline of person but is filled with an illuminating light, but does not include any facial expressions (e.g., nose, hair, eyes etc.) or any emotional facial expressions (e.g., sadness, happiness, etc.). Thus, for example, the illuminating light may range in brightness. For example, the illuminating light inside the light being may be a soft light, such as less than 2,000 Kelvins. In embodiments, the user may change the light intensity of the light being. Thus, if the user wishes to have a different light level, the user may decide to have the light being with a light level of between 2,000 to 3,000 Kelvins. In embodiments, the color of the light being may be adjusted by the user. For example, the color may be a white color, a yellow color, a blue color, a pink color, or any other color.

While a user may change the features of the light being, the light being's features may be changed based on the interaction with the user's generated electronic character. For example, if the user has selected "sad" to be associated with the user's generated electronic character, then the electronic application may generate a light being that is of a particular light level (e.g., Kelvins) and also a particular color. As such, if the user has selected "angry," then the electronic application may generate a light being that is of a particular light level and a particular color that is different from when the electronic application generated the light being with the color and light level for the "sad" emotion. Thus, the electronic application may determine the color and light level of the light being based on the user's inputs for the user's generated electronic character.

In embodiments, once the user's generated electronic character has changed its emotional state (as displayed via the electronic application), the light being may change its color and light level too. For example, the light being may become lighter in light intensity and/or change its color. In embodiments, the light being does not have facial expressions (e.g., nose, eyes, ears), and/or any emotional expressions (e.g., happiness, sadness, etc.).

Once the light being is created, the display may show the user's generated electronic character and the light being on the same display. In a non-limiting example, the user may choose a particular word that generates an electronic expression on the user's generated electronic character. For example, if the user had chosen the word "anxious," the light being may demonstrate a particular animations associated with "The Butterfly Hug." Accordingly, the electronic character will electronically move in the same manner as the light being and the electronic character's electronic features may change. In embodiments, the user may copy the electronic character's electronic movements to assist in improving the user's own emotional state.

In embodiments, the electronic application have other icons that may include an icon that if selected will generate an electronic page that includes mental health professionals that are within a particular geographic distance from the user (based on the user's location, zip code, address, etc.) In embodiments, the electronic application may allow the user to provide further information for the user, including ethnicity, race, sexuality, age, religious affiliation, and insurance that may be used by the therapist. In embodiments, the user can communicate with the therapist via the electronic communication via a chat bubble and a calendar to schedule an appointment with the mental health professional. Accordingly, the mental health professional can limit the user's issues relating to their psychological situation.

In embodiments, the electronic application may include additional icons that when selected provide the user with the ability to contact emergency services and/or hotlines (e.g., such as the National Suicide Prevention Hotline and the Substance Abuse and Mental Health Services Administration National Helpline).

Figure 1B:
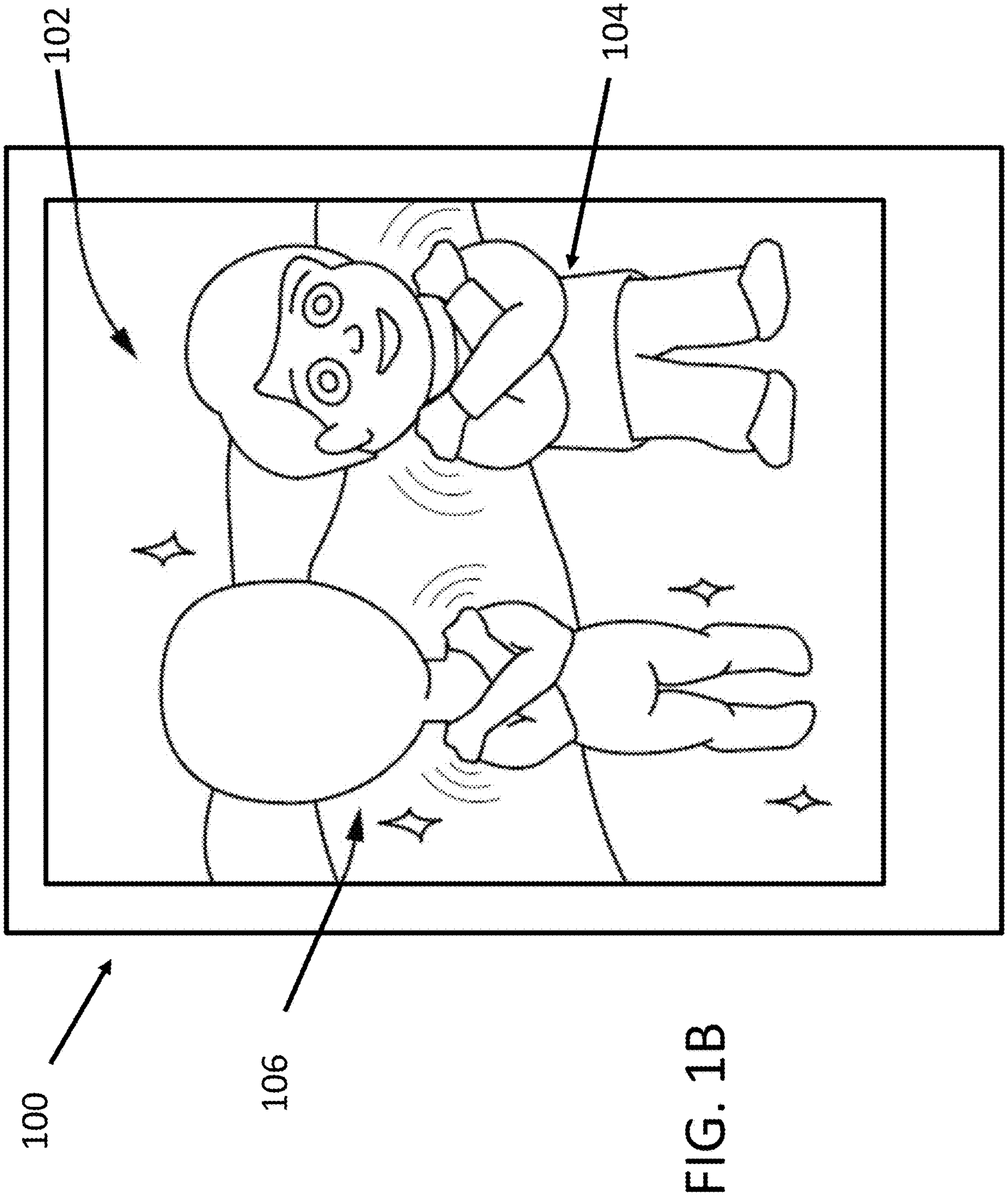

FIGS. 1A-1B shows diagrams of an example environment in which systems and/or methods described herein may be implemented. FIG. 1A shows a device 100 that has a display 102 which includes an electronic image of a character 104 of a person using device 100. In this non-limiting example, character 104 has been created based on one or more inputs from a user of device 100. Once character 104 is generated and displayed on display 102, light character 106 is also generated and appears on the same electronic display as character 104. In addition to generating character 104, a user is also requested to provide a word that describes how they are feeling. In this non-limiting example, the user selects "anxious."

In this non-limiting example, light character 106 may initiate an electronic communication with character 104 which is displayed to the user of device 100. For the state of being anxious, light character may electronically communicate a butterfly hug. As shown in FIG. 1B, light character 106 generates a voice communication which results in character 104 becoming animated and displaying a butterfly hug. Accordingly, the user of device 100 decides to copy the image of character 104. In this non-limiting example, the electronic communication of light character 106, via communication with character 104, resolves the user's anxious condition. Thus, the user of device 100 does not make additional electronic communications via a computer, the device, or a telephone for a particular amount of time since the user has been calmed down for that particular amount of time.

Thus, as shown in FIGS. 1A and 1B, an individual having a mental condition can be controlled by the electronic interactions between two electronic characters. And, by controlling a person's mental condition, immediate electronic communications with a medical professional at a different geographic location is delayed.

Figure 2:
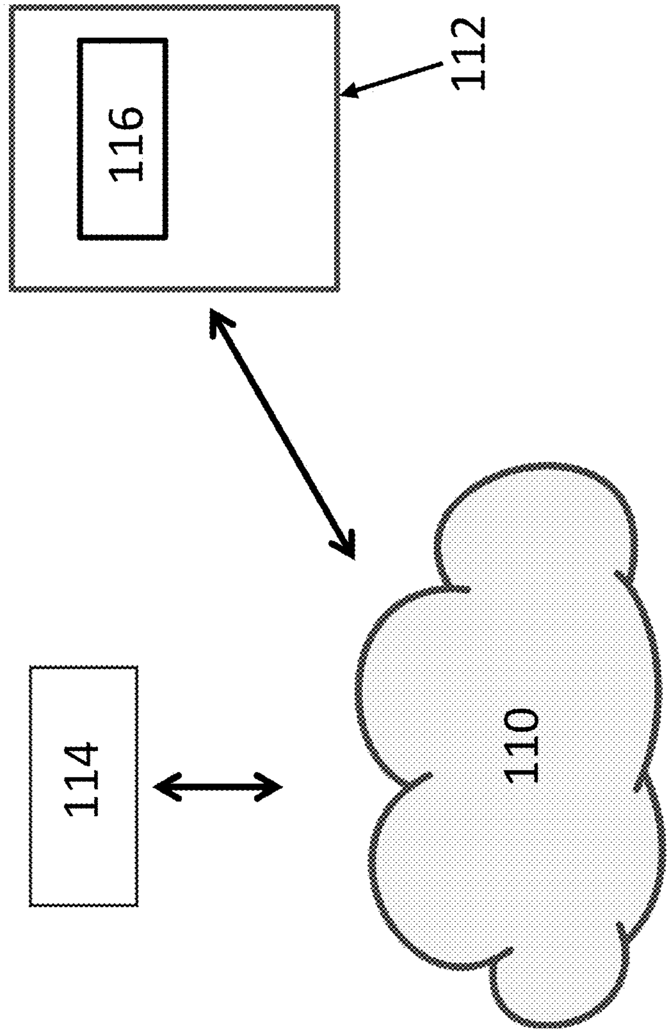
FIG. 2 is a diagram of a network environment.

FIG. 2 is a diagram of example environment 200 in which systems, devices, and/or methods described herein may be implemented. FIG. 2 shows network 110, user device 112, server 114, and electronic application 116.

Network 110 may include a local area network (LAN), wide area network (WAN), a metropolitan network (MAN), a telephone network (e.g., the Public Switched Telephone Network (PSTN)), a Wireless Local Area Networking (WLAN), a WiFi, a hotspot, a Light fidelity (LiFi), a Worldwide Interoperability for Microware Access (WiMax), an ad hoc network, an intranet, the Internet, a satellite network, a GPS network, a fiber optic-based network, and/or combination of these or other types of networks. Additionally, or alternatively, network 110 may include a cellular network, a public land mobile network (PLMN), a second generation (2G) network, a third generation (3G) network, a fourth generation (4G) network, a fifth generation (5G) network, and/or another network. In embodiments, network 110 may allow for devices describe any of the described figures to electronically communicate (e.g., using emails, electronic signals, URL links, web links, electronic bits, fiber optic signals, wireless signals, wired signals, etc.) with each other so as to send and receive various types of electronic communications.

User device 112 may include any computation or communications device that is capable of communicating with a network (e.g., network 110). For example, user device 112 may include a radiotelephone, a personal communications system (PCS) terminal (e.g., that may combine a cellular radiotelephone with data processing and data communications capabilities), a personal digital assistant (PDA) (e.g., that can include a radiotelephone, a pager, Internet/intranet access, etc.), a smart phone, a desktop computer, a laptop computer, a tablet computer, a camera, a personal gaming system, a television, a set top box, a digital video recorder (DVR), a digital audio recorder (DUR), a digital watch, a digital glass, or another type of computation or communications device.

User device 112 may receive and/or display content. The content may include objects, data, images, audio, video, text, files, and/or links to files accessible via one or more networks. Content may include a media stream, which may refer to a stream of content that includes video content (e.g., a video stream), audio content (e.g., an audio stream), and/or textual content (e.g., a textual stream). In embodiments, an electronic application may use an electronic graphical user interface to display content and/or information via user device 112 and/or 114. User device 112 may have a touch screen and/or a keyboard that allows a user to electronically interact with an electronic application. In embodiments, a user may swipe, press, or touch user device 112 in such a manner that one or more electronic actions will be initiated by user device 112 via an electronic application.

User device 112 may include a variety of applications, such as, for example, electronic application 116, electronic coping application, an e-mail application, a telephone application, a camera application, a video application, a multimedia application, a music player application, a visual voice mail application, a contacts application, a data organizer application, a calendar application, an instant messaging application, a texting application, a web browsing application, a blogging application, and/or other types of applications (e.g., a word processing application, a spreadsheet application, etc.).

Electronic application 116 may be capable of interacting with user device 112 and/or server 114 to automatically and electronically receive electronic information for one or more persons. In embodiments, electronic application 116 may obtain electronic information about a person's identity, such as name, address, age, profession, hair color, eye color, skin color, and/or any other type of information. In embodiments, electronic application 116 may be electronically configured to show photos, video, text, icons, graphical images, buttons, emojis, and/or any other electronic information. In embodiments, electronic application 116 may generate electronic characters with emotional expressions that can be changed. In embodiments, electronic application 116 may generate an electronic light being (as described above) that can interact with an electronic character and change the electronic character's emotion as displayed via electronic application 116. While FIG. 2 shows electronic application 116 on user device 112, some or all of the electronic processes performed by electronic application 116 may be stored by server 114.

Server 114 may include one or more computational or communication devices that gather, process, store, and/or provide information relating to one or more electronic pages associated with electronic application 116 that is searchable and viewable over network 110. While FIG. 2 shows one server 114, there may be additional servers 114 associated with one or more electronic applications 116. In embodiments, server 114 may receive electronic information based on a person's physical characteristics and definitions associated with a person's mental condition. In embodiments, geographic location information may include street number, street name, street type, village, town, city, county, state, and/or country information.

Figure 3:
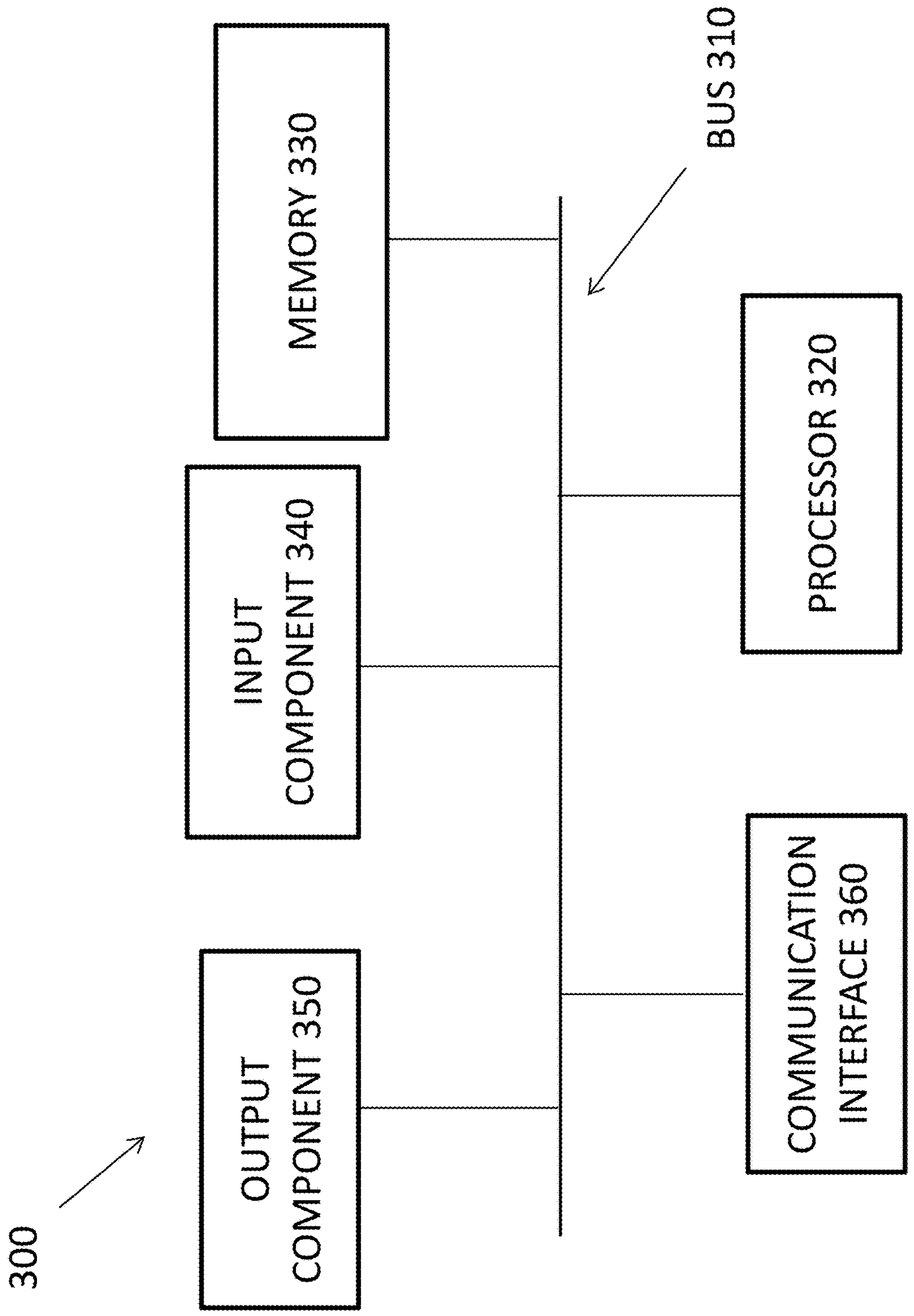
FIG. 3 is a diagram of an example computing device.

FIG. 3 is a diagram of example components of a device 300. Device 300 may correspond to user device 112 and server 114. Alternatively, or additionally, user device 112 and server 114 may include one or more devices 300 and/or one or more components of device 300.

As shown in FIG. 3, device 300 may include a bus 310, a processor 320, a memory 330, an input component 340, an output component 350, and a communications interface 360. In other implementations, device 300 may contain fewer components, additional components, different components, or differently arranged components than depicted in FIG. 3. Additionally, or alternatively, one or more components of device 300 may perform one or more tasks described as being performed by one or more other components of device 300.

Bus 310 may include a path that permits communications among the components of device 300. Processor 320 may include one or more processors, microprocessors, or processing logic (e.g., a field programmable gate array (FPGA) or an application specific integrated circuit (ASIC)) that interprets and executes instructions. Memory 330 may include any type of dynamic storage device that stores information and instructions, for execution by processor 320, and/or any type of non-volatile storage device that stores information for use by processor 320. Input component 340 may include a mechanism that permits a user to input information to device 300, such as a keyboard, a keypad, a button, a switch, voice command, etc. Output component 350 may include a mechanism that outputs information to the user, such as a display, a speaker, one or more light emitting diodes (LEDs), etc.

Communications interface 360 may include any transceiver-like mechanism that enables device 300 to communicate with other devices and/or systems. For example, communications interface 360 may include an Ethernet interface, an optical interface, a coaxial interface, a wireless interface, or the like.

In another implementation, communications interface 360 may include, for example, a transmitter that may convert baseband signals from processor 320 to radio frequency (RF) signals and/or a receiver that may convert RF signals to baseband signals. Alternatively, communications interface 360 may include a transceiver to perform functions of both a transmitter and a receiver of wireless communications (e.g., radio frequency, infrared, visual optics, etc.), wired communications (e.g., conductive wire, twisted pair cable, coaxial cable, transmission line, fiber optic cable, waveguide, etc.), or a combination of wireless and wired communications.

Communications interface 360 may connect to an antenna assembly (not shown in FIG. 3) for transmission and/or reception of the RF signals. The antenna assembly may include one or more antennas to transmit and/or receive RF signals over the air. The antenna assembly may, for example, receive RF signals from communications interface 360 and transmit the RF signals over the air, and receive RF signals over the air and provide the RF signals to communications interface 360. In one implementation, for example, communications interface 360 may communicate with network 110.

As will be described in detail below, device 300 may perform certain operations. Device 300 may perform these operations in response to processor 320 executing software instructions (e.g., computer program(s)) contained in a computer-readable medium, such as memory 330, a secondary storage device (e.g., hard disk, CD-ROM, etc.), or other forms of RAM or ROM. A computer-readable medium may be defined as a non-transitory memory device. A memory device may include space within a single physical memory device or spread across multiple physical memory devices. The software instructions may be read into memory 330 from another computer-readable medium or from another device. The software instructions contained in memory 330 may cause processor 320 to perform processes described herein. Alternatively, hardwired circuitry may be used in place of or in combination with software instructions to implement processes described herein. Thus, implementations described herein are not limited to any specific combination of hardware circuitry and software.

Figure 4:
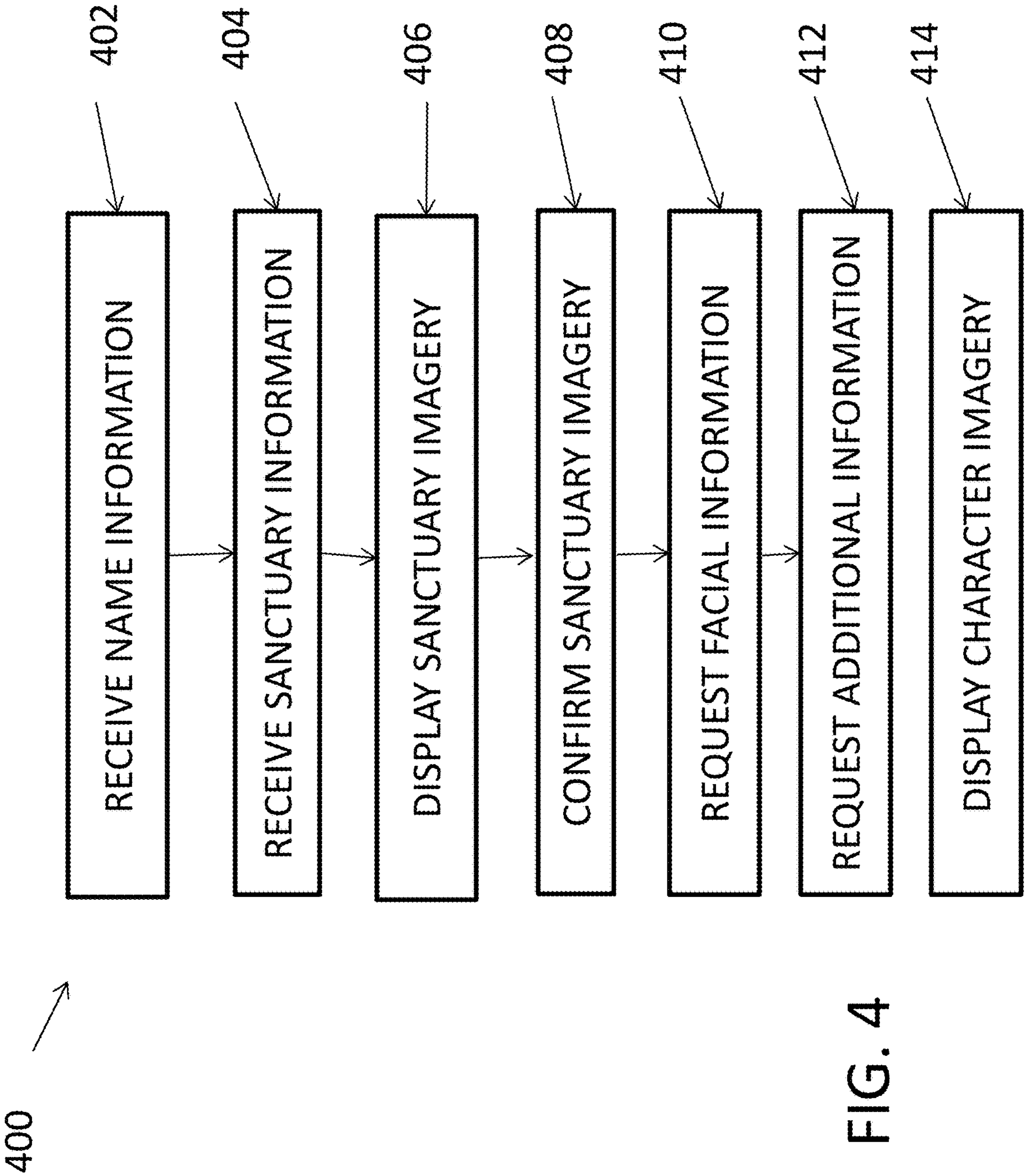
FIG. 4 is an example flow diagram.

FIG. 4 describes an example flow diagram 400 for generating an electronic character (e.g., such as character 104). Flow diagram 400 may be conducted by user device 112 and/or electronic application 116. In embodiments, electronic application 116 downloaded onto user device 112.

As shown in FIG. 4, at step 402, device 112 and/or electronic application 116 may request a user to enter his/her/their name. In embodiments, the user may enter their name. At step 404, device 112 and/or electronic application 116 may request the user to provide imagery for a sanctuary. In embodiments, the sanctuary imagery may be imagery that is considered by the user to be a safe place. For example, the sanctuary imagery may be a beach, a forest pathway, a bedroom, a bookstore, or any other place of comfort as determined by the user. In embodiments, device 112 and/or electronic application 116 may request the user to electronically input one or more words that describes their concept of a sanctuary. In alternate embodiments, device 112 and/or electronic application 116 may display icons with imagery associated with different types of sanctuaries.

In embodiments, device 112 and/or electronic application 116 receive electronic information about the sanctuary. At step 406, device 112 and/or electronic application 116 may display a proposed sanctuary imagery. In embodiments, device 112 and/or electronic application 116 may receive acceptance of the sanctuary imagery or may request different imagery. Once a sanctuary image is selected, at step 408, the selected sanctuary imagery is displayed. At step 410, device 112 and/or electronic application 116 may request electronic information about the user's facial characteristics. In embodiments, device 112 and/or electronic application 116 may initially display a blank face image. In alternate embodiments, device 112 and/or electronic application 116 may request the user provide verbal or word inputs without no display any blank facial imagery.

In embodiments, device 112 and/or electronic application 116 may receive electronic information from the user which includes hair color, hair texture, hair style, skin color, skin texture, and nose shape. In embodiments, the user may enter any electronic information that makes them feel comfortable rather than what the user actually looks like. Thus, the character image associated with the user may not look like the user. Accordingly, device 112 and/or electronic application 116 may generate an electronic image that is different from the user. Thus, a user has the option to choose their character style.

At step 412, device 112 and/or electronic application 116 may request additional information about the user. In embodiments, device 112 and/or electronic application 116 may request if the user wishes to provide body information. If the user decides not to provide body information, then device 112 and/or electronic application 116 may generate a character image that is only the face. However, if the user decides to provide body information, then device 112 and/or electronic application 116 may generate a character image that includes a full character with body and facial features. In embodiments, device 112 and/or electronic application 116 may receive body (such as weight dimensions), height, gender, clothing type, skin color, and/or any other information. In embodiments, device 112 and/or electronic application 116 may receive an uploaded photo or image of the user and generate an electronic character based on the uploaded photo or image.

At step 414, device 112 and/or electronic application 116 may generate an electronic character. In embodiments, device 112 and/or electronic application 116 may display the electronic character in the sanctuary image.

Figure 5:
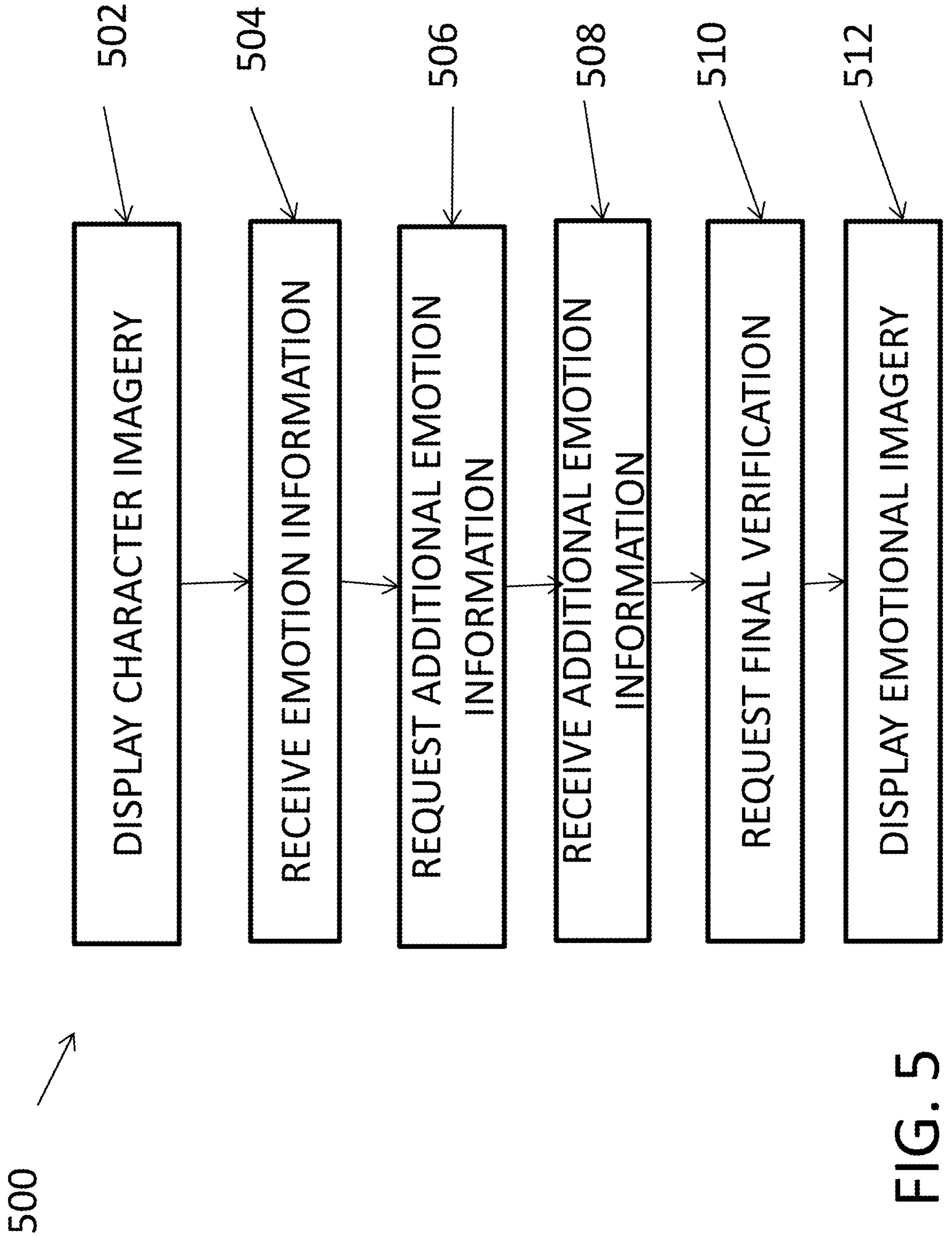
FIG. 5 is an example flow diagram.

FIG. 5 is an example flow diagram 500. In embodiments, flow diagram 500 may be conducted by device 112 and/or electronic application 116. At step 502, an electronic character (such as generated by the process described in FIG. 4) is displayed on device 112 via electronic application 116. In embodiments, the electronic character is displayed along with one or more electronic icons. In embodiments, the electronic icons may be associated with different electronic communication features in electronic application 116.

In embodiments, one of the icons is associated with selecting an emotional feature that will be associated with the electronic character. In embodiments, the emotion icon may be designed as a wheel. In alternate embodiments, the emotion icon may be designed in a different shape. In embodiments, another icon may provide the user with a list of therapists if selected. In embodiments, the icon associated with selecting therapists may be designed as a heart shaped icon. In embodiments, the third icon may be an emergency icon that can contact emergency services (e.g., 911) when selected.

At step 504, device 112 and/or electronic application 116 may receive an electronic communication based on selection of the emotion icon. In a non-limiting example, the selection of the emotion icon may be associated with the sad emotion. At step 506, device 112 and/or electronic application 116 may request additional information about the selected emotion in Step 504 by displaying a secondary emotion icon. In embodiments, the secondary emotion icon may request further description of the emotion being felt by the user. At step 508, device 112 and/or electronic application 116 may receive additional information about the selected emotion in Step 504. At step 510, device 112 and/or electronic application 116 may request a final verification that the additional information describes the user's current emotional state. In embodiments, the user may provide further information or may send a communication to device 112 and/or electronic application 116 that the additional information describes the user's current emotional state.

At step 512, device 112 and/or electronic application 116 may change the electronic character's displayed features to show a final emotional state imagery on the electronic character, based on what is described in steps 506 to 510.

Figure 6:
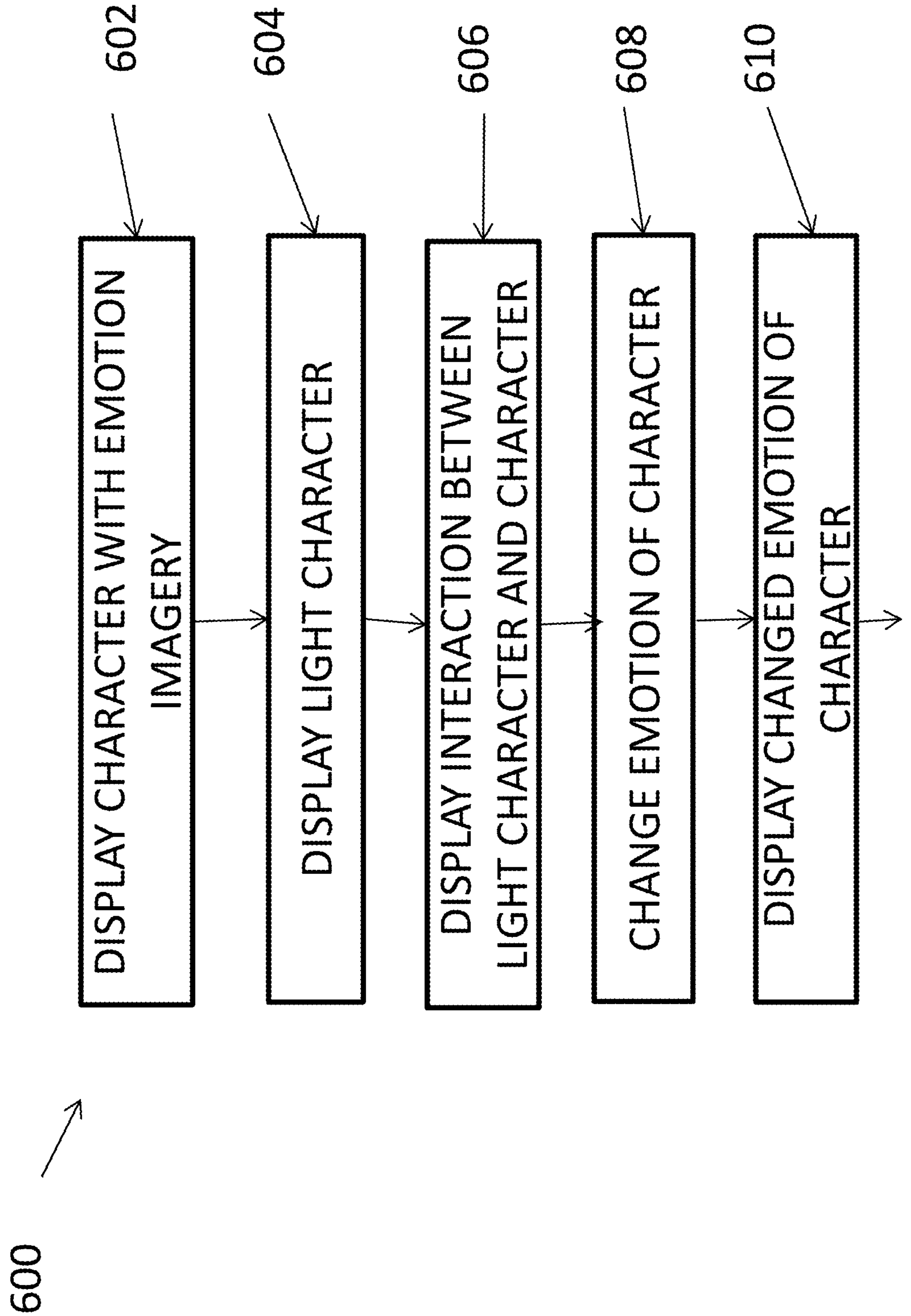
FIG. 6 is an example flow diagram.

FIG. 6 shows an example flow diagram 600. In embodiments, flow diagram 600 may be conducted by device 112 and/or electronic application 116. At 602, an electronic character (such as generated by the process described in FIG. 5) is displayed with a particular emotion (such as generated by the process described in FIG. 6). At 604, device 112 and/or electronic application 116 may electronically display a light character. In embodiments, the light character is an electronic feature of electronic application that interacts with the electronic character to electronically change the emotional state of the electronic character. In embodiments, the light character may be displayed with a particular color light that reduces one or more communications by the user via device 112 for a particular amount of time. For example, without viewing the light character, device 112 may receive a communication within five minutes; however, by viewing the light character, device 112 may receive an electronic communication 30 minutes later from the user as the user does not need to immediately communicate with a therapist.

At step 606, the light character interacts with the electronic character. In embodiments, the light character. In embodiments, the light character may graphically change its shape as it is communicating with the electronic character. For example, the light character may change shape such as expand and contract as it provides an electronic communication that is audible to the user. Or, for example, the light character may change colors at it is communicating with the electronic character. In embodiments, any electronic communication between the electronic character and the light character may be shown to the user by sounds (e.g., voice characterization) or textual display. In embodiments, the light character may display physical action, such as hugging or massaging, etc.

At step 608, the electronic character changes its graphical features based on the interaction between the light character and the electronic character. In embodiments, the electronic character electronic body features may change based on the light character's electronically displayed actions. For example, if the light character electronically displays a hugging action, the electronic character may electronically perform the same hugging action.

At step 610, the electronic character's mental state changes. In embodiments, the electronic character's mental state change is shown by a different electronic face feature or changes to other electronic features such as the electronic character's skin color, a change to color or design of the sanctuary background, and/or any other features.

Figure 7A:
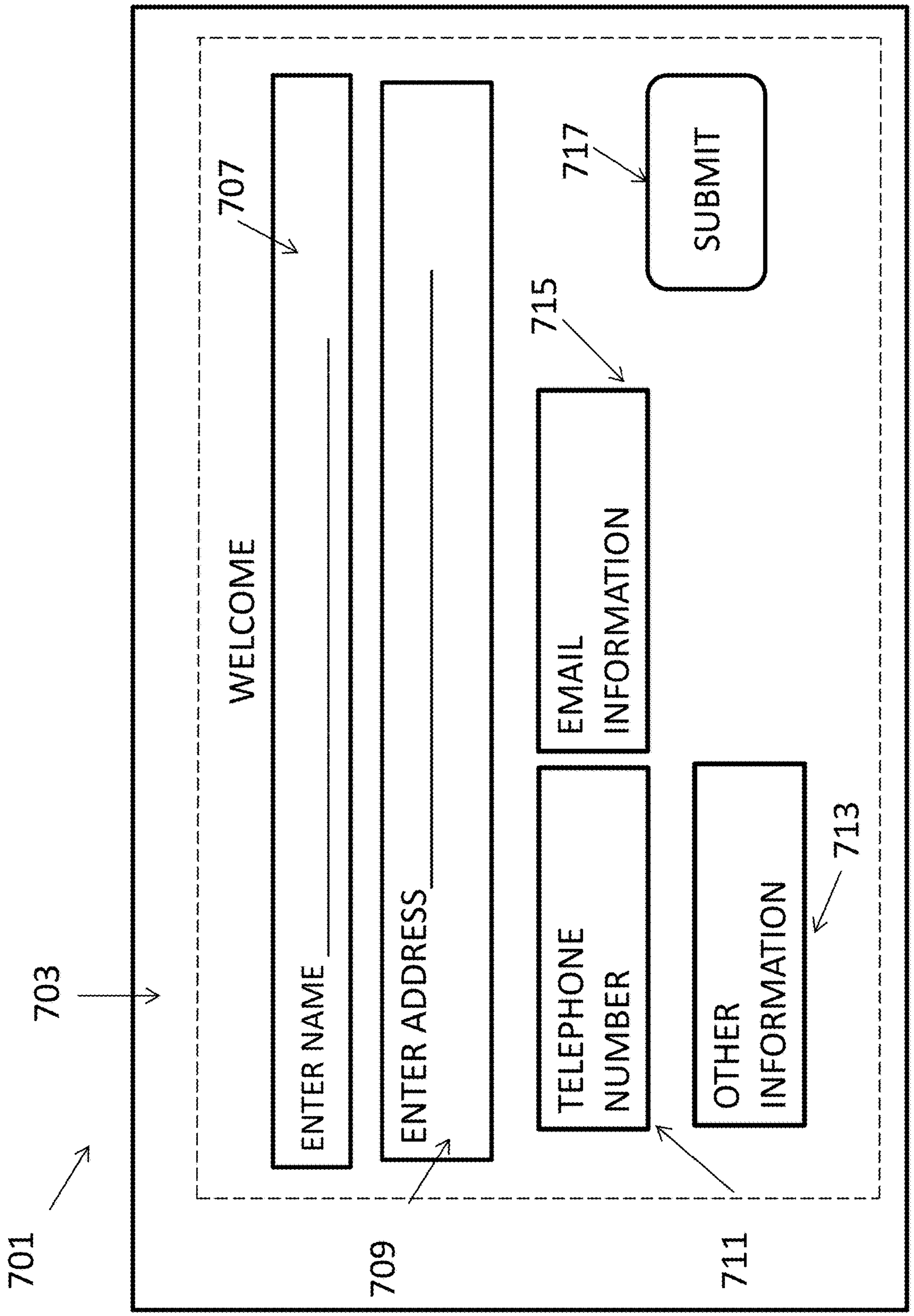
FIGS. 7A-7H are diagrams for an example communication process.
Figure 7B:
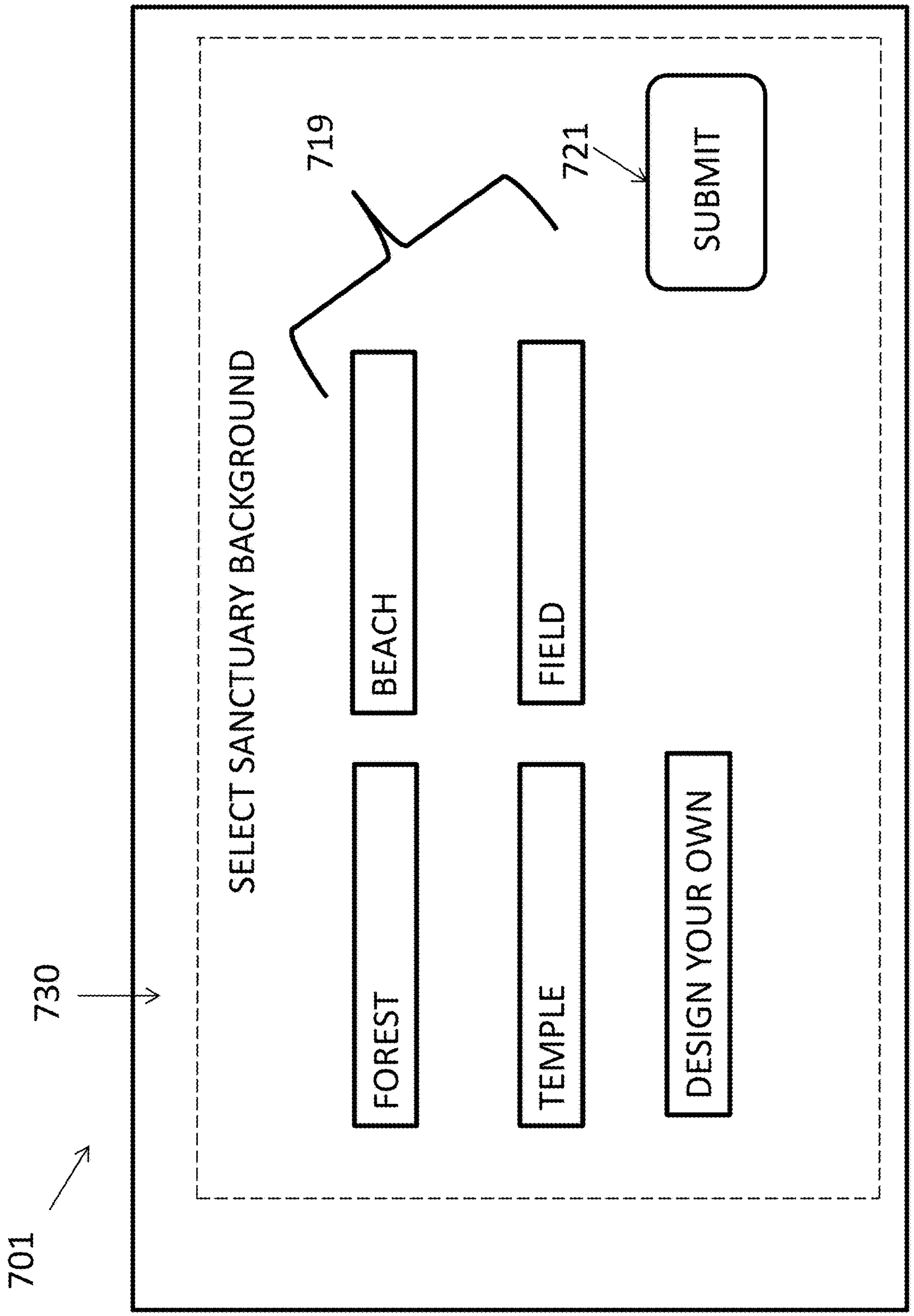
Figure 7C:
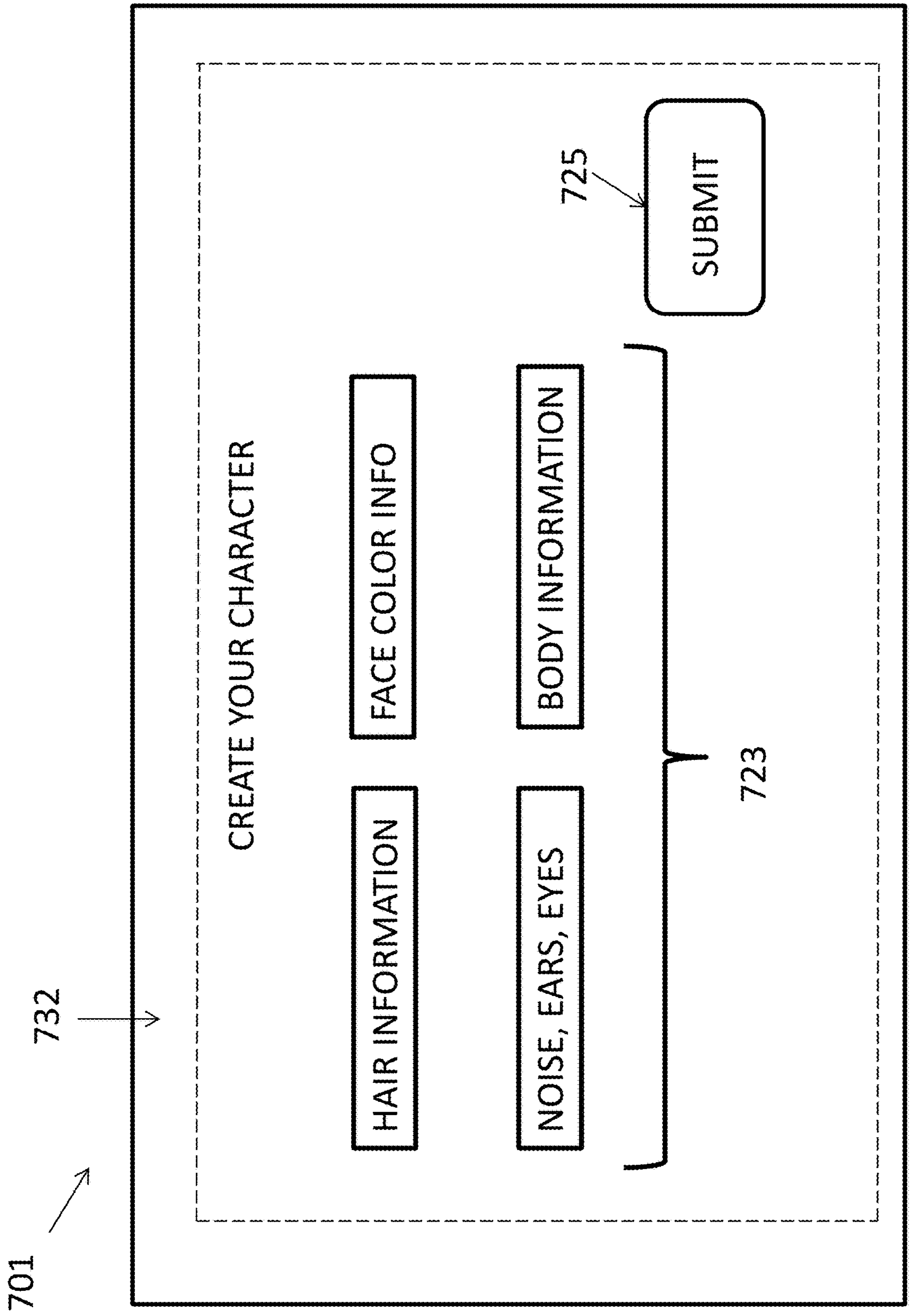
Figure 7D:
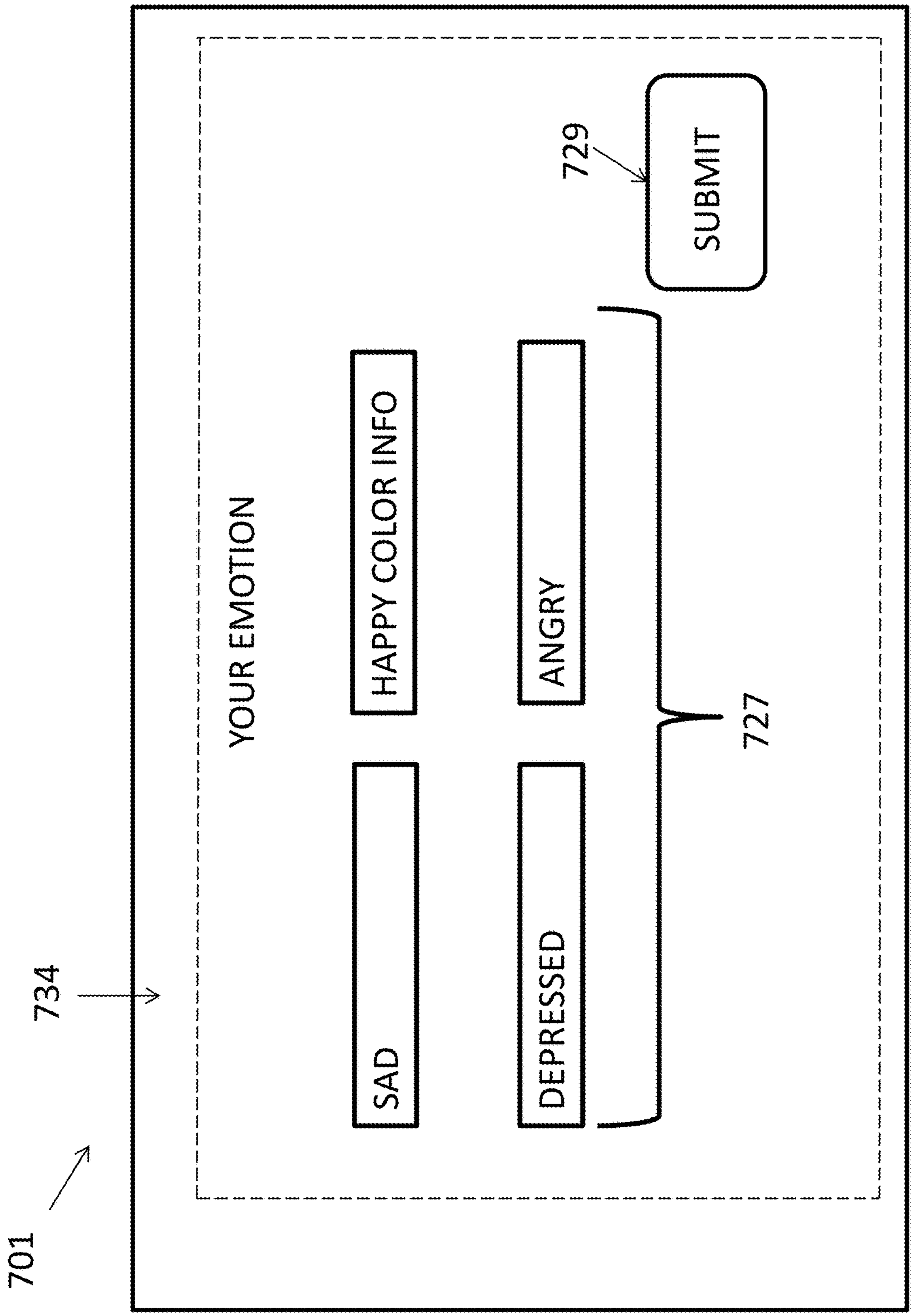

FIG. 7A-7H Show an example process for creating an electronic coping interaction. As shown in FIG. 7A, an introduction page 703 for an electronic application is displayed on device 701. As shown, the introduction page requests a user to input their name, address, and/or telephone number in electronic areas 707, 709, 711, 713, and 713. This information is then electronically submitted by submit button 715. As shown in FIG. 7B, once the user has inputted the information, electronic application 702 requests the user to select a sanctuary background via electronic page 730. As shown in FIG. 7B, a user may make selections from one or more fields in fields 719. As shown in FIG. 7B, in this non-limiting example, three selections are provided with two that pre-designed backgrounds and one that provides an option to design a custom background. Once selected, the selections are electronically saved by the selection of submit button 721. As shown in FIG. 7C, the electronic application requests information that will be used to create an electronic character via electronic page 732. In this non-limiting example, electronic application 702 requests skin color information, hair information, clothing information, head covering information, and/or any other information for the electronic application by the user selecting one or more fields from fields 723. Once selected, the selections are electronically saved by the selection of submit button 725. As shown in FIG. 7D, electronic application 702 asks what mood should be associated with an electronic character (which may be similar to the mood of the user of user device 700) via electronic page 734. As shown in FIG. 7D, electronic application 702 may display several options from fields 727. Once selected, electronic application 702 may display additional options to further define the mood to be associated with an electronic character. Once selected, the selections are electronically saved by the selection of submit button 729. In embodiments, electronic page 734 may display an emotion wheel which includes the option to make selection of all emotional information on a single page.

Figure 7E:
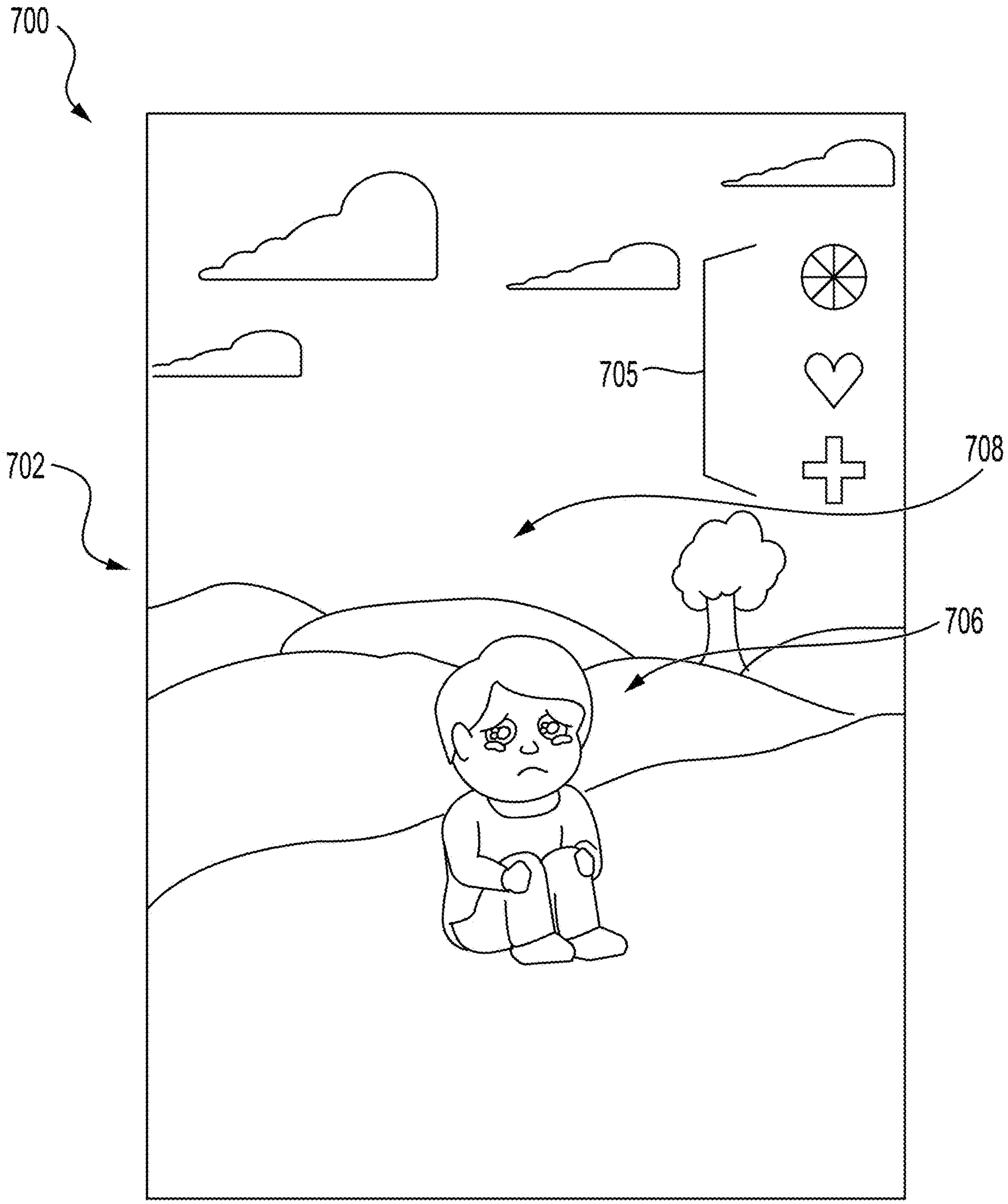
Figure 7F:
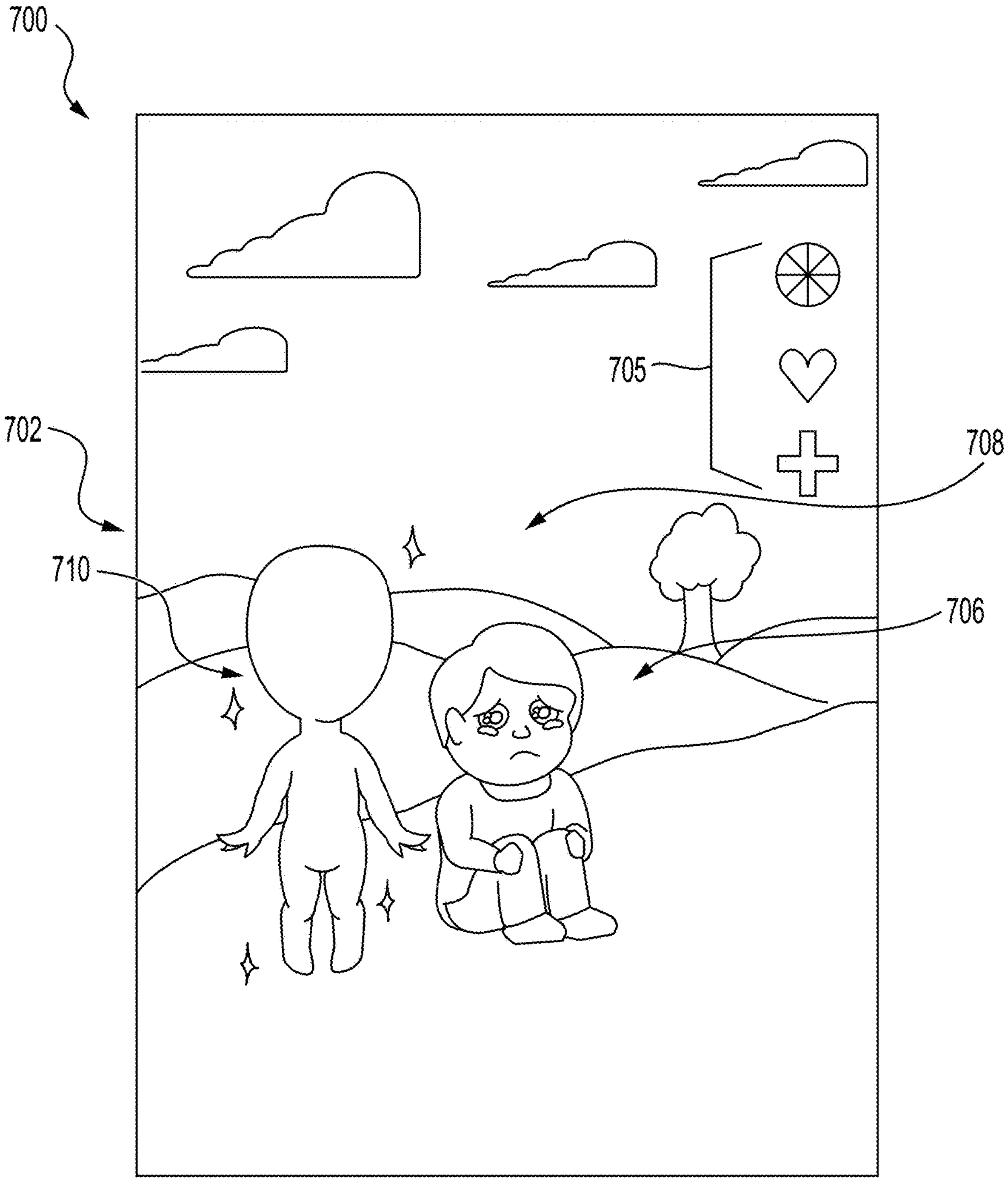
Figure 7G:
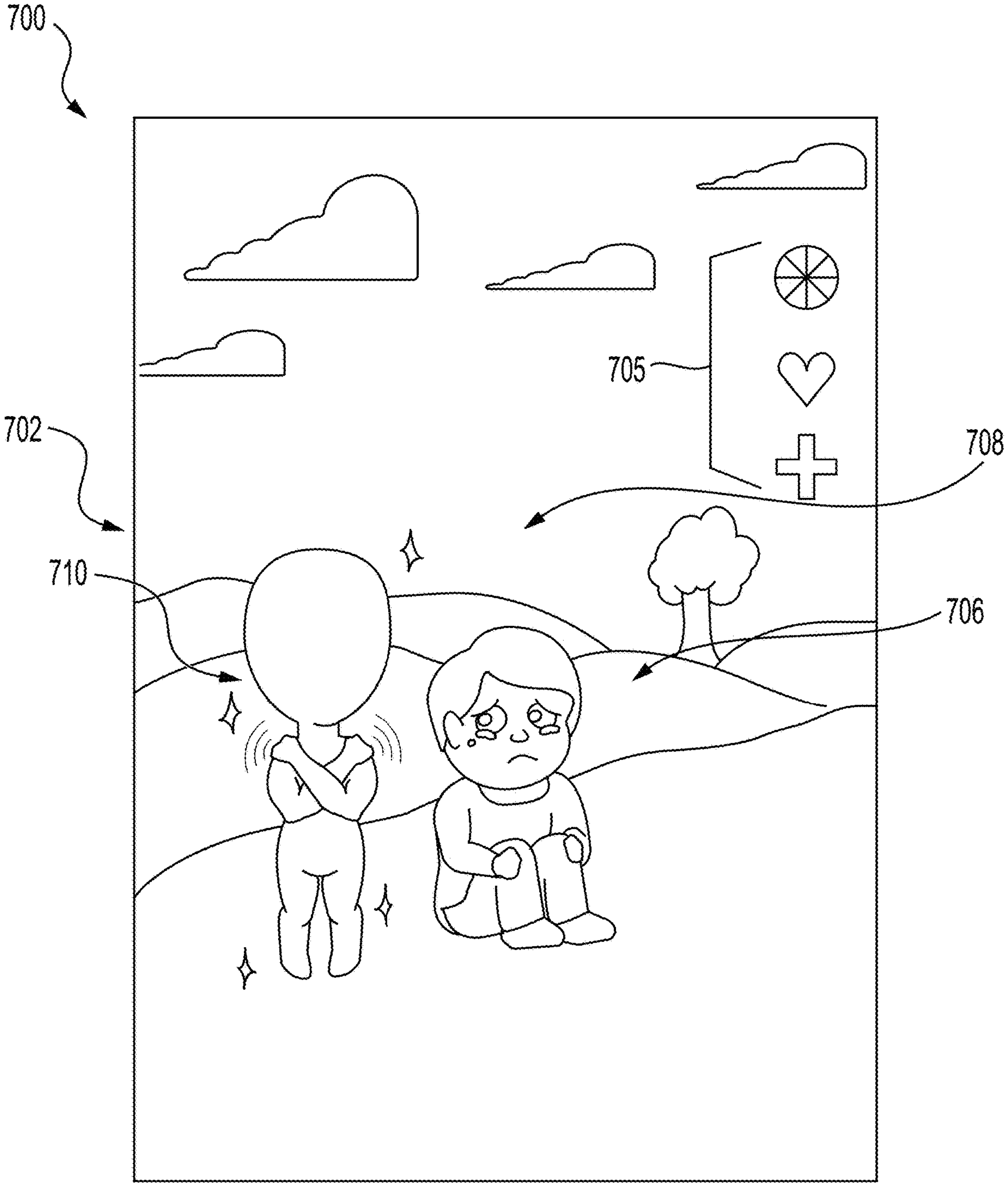
Figure 7H:
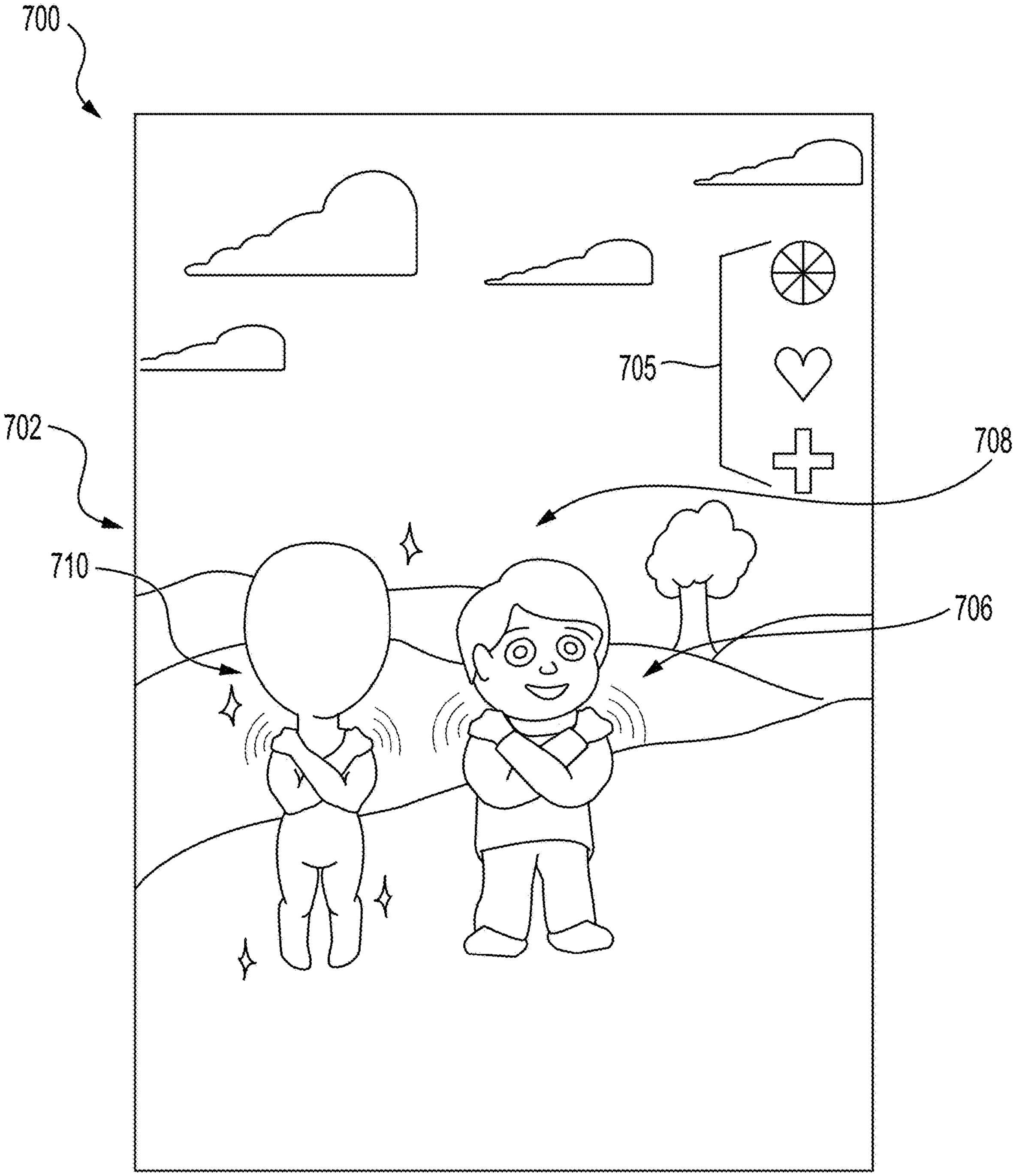

Once a sanctuary background, electronic character features, and electronic features are saved with the electronic application (e.g., electronic application 116) and can be used by the electronic application to assist a user with their emotional state. As shown in FIG. 7E, via electronic application (e.g., electronic application 116), electronic character 706 (based on the information inputted into electronic application as described in FIGS. 7C and 7D) is displayed on sanctuary background 708. In this non-limiting example, electronic application 702 requests confirmation which it receives. As shown in FIG. 7F, via the electronic application (e.g., electronic application 116), light character 710 (similar to the light character discussed in FIG. 6 and/or discussed as a light being above) is displayed along with electronic character 706. As shown in FIG. 7G, via the electronic application (e.g., electronic application 116), light character 710 changes it shape to show a hugging action. As shown in FIG. 7H, via the electronic application (e.g., electronic application 116), electronic character 706 electronically copies the movements of light character 710. Also, as shown FIGS. 7E to 7G, icons 705 are also shown.

One of icons 705 may be selected by a user of electronic application 702. One of the icons, such as the cross icon, if selected may generated an electronic communication (e.g., such as a 911 communication) from electronic application 702 and a computing device associated with a hospital/medical center. One of the other icons, such as the heart icon, if selected may generate an electronic communication (and also an electronic page) to a therapist, such as the user's personal therapist. One of the other icons, such as the wheel icon, if selected may generate an electronic page with an electronic emotional wheel that has one or more features that when selected generate an emotion that is shown by electronic character 706. In embodiments, an electronic communication to a hospital/medical center or therapist may occur in a particular time after the electronic character's emotional state has changed. However, the electronic communication to a hospital/medical center or therapist may occur at any time (e.g., such as before the display of light character 710).

While FIGS. 7A-7H describe an example where electronic application 702 generates a light character to help a user of electronic application 702 to cope with a mental issue, in other examples electronic application 702 may display an electronic emergency communication. For example, if a user inputs the word "suicide" or similar text, electronic application 702 may automatically contact emergency services (such as the police, hospital, etc.) via an electronic communication or via an electronic communications to a call center which then contacts local authorities.

Even though particular combinations of features are recited in the claims and/or disclosed in the specification, these combinations are not intended to limit the disclosure of the possible implementations. In fact, many of these features may be combined in ways not specifically recited in the claims and/or disclosed in the specification. Although each dependent claim listed below may directly depend on only one other claim, the disclosure of the possible implementations includes each dependent claim in combination with every other claim in the claim set.

While various actions are described as selecting, displaying, transferring, sending, receiving, generating, notifying, and storing, it will be understood that these example actions are occurring within an electronic computing and/or electronic networking environment and may require one or more computing devices, as described in FIG. 2, to complete such actions. Furthermore, it will be understood that these various actions can be performed by using a touch screen on a computing device (e.g., touching an icon, swiping a bar or icon), using a keyboard, a mouse, or any other process for electronically selecting an option displayed on a display screen to electronically communicate with other computing devices as described in FIG. 2. It will be understood that time information includes time, day, month, and/or year information and may be an electronic time stamp. Also, it will be understood that any of the various actions can result in any type of electronic information to be displayed in real-time and/or simultaneously on multiple user devices. For FIGS. 4, 5, and 6, the order of the blocks may be modified in other implementations. Further, non-dependent blocks may be performed in parallel.

No element, act, or instruction used in the present application should be construed as critical or essential unless explicitly described as such. Also, as used herein, the article "a" is intended to include one or more items and may be used interchangeably with "one or more." Where only one item is intended, the term "one" or similar language is used. Further, the phrase "based on" is intended to mean "based, at least in part, on" unless explicitly stated otherwise.

In the preceding specification, light character and light being are used interchangeably and are electronic features as discussed above. In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

What is claimed is:

1. An electronic communications method, comprising:
generating, by a computing device, a displayable background area, wherein the displayable background area is selected from one of:
a beach background,
a forest background,
a pathway background,
a bedroom background, and
a bookstore background;
receiving, by the computing device, a request to generate an electronic character;
receiving, by the computing device, an electronic communication that includes information about different features of the electronic character;
generating, by the computing device, an electronic character that includes the different features, wherein the different features of the electronic character include:
facial expressions,
facial features including a nose, eyes, and a mouth, and
a particular electronically generated emotion;
displaying, by the computing device, the electronic character;
generating, by the computing device, an electronic light being;
displaying, by the computing device, the electronic light being at the same time that the electronic character is being displayed, wherein:
the electronic character and the electronic light being are displayed within the displayable background area;
the electronic character and the electronic light being, when displayed, in separate areas of the displayable background area,
the electronic light being does not have any facial expressions or facial features,
the electronic light being has a level of displayable light that is adjustable,
wherein the adjustability of the displayable light is based on the particularly electronically generated emotion of the electronic character, and the electronic light being is generated based on electronic inputs;
generating, by the computing device, an action by the electronic light being;
changing, by the computing device, the level of displayable light based on the action of the electronic light being;
automatically contracting, by the computing device, the electronic light being size at the same time that the electronic light being generates an electronic audible communication, wherein the contracted size of the electronic light being and the electronic audible communication occur based on the changing the level of displayable light of the electronic light being;
automatically generating, by the computing device, the same action by the electronic character;
automatically changing, by the computing device, the displayable background area based on the generated emotion of the electronic character;
automatically changing, by the computing device, the electronically generated emotion of the electronic character based on the action of the electronic light being; and,
receiving, by the computing device, after a time delay, another electronic communication that is then sent to another computing device associated with a therapist.

2. The electronic communications method of claim 1, wherein the level of displayable light is of a particular color.

3. The electronic communications method of claim 1, wherein the another electronic communication is sent via selection of an icon.

4. The electronic communications method of claim 3, wherein the icon is associated with an electronic emotional wheel.

5. The electronic communication method of claim 3, wherein the icon is associated with a medical facility.

6. The electronic communications method of claim 1, further comprising: adjusting, by the computing device, the electronic light being's shape when the electronic light being is electronically communicating with the electronic character, wherein the electronic light being's shape can expand.

7. A device, comprising:
memory; and
a processor to:
generate a displayable background area, wherein the displayable background area is selected from one of:
a beach background,
a forest background,
a pathway background,
a bedroom background, and
a bookstore background;
receive a request to generate an electronic character;
receive an electronic communication that includes information about different features of the electronic character;
generate an electronic character that includes the different features, wherein the different features of the electronic character include:
facial expressions,
facial features including a nose, eyes, and a mouth, and
a particular electronically generated emotion;
display the electronic character;
generate an electronic light being;
display the electronic light being at the same time that the electronic character is being displayed, wherein:
the electronic character and the electronic light being are displayed within the displayable background area,
the electronic character and the electronic light being, when displayed, in separate areas of the displayable background area,
the electronic light being does not have any facial expressions or facial features,
the electronic light being has a level of displayable light that is adjustable,
wherein the adjustability of the displayable light is based on the particularly electronically generated emotion of the electronic character, and the electronic light being is generated based on electronic inputs;
generate an action by the electronic light being;

change the level of displayable light based on the action of the electronic light being;

automatically contract the electronic light being size at the same time that the electronic light being generates an electronic audible communication, wherein the contracted size of the electronic light being and the electronic audible communication occur based on the changing the level of displayable light of the electronic light being;

automatically generate the same action by the electronic character;

automatically change the displayable background area based on the generated emotion of the electronic character; and change the electronically generated emotion of the electronic character based on the action of the electronic light being.

8. A non-transitory computer-readable medium storing instructions, the instructions comprising:

one or more instructions that, when executed by one or more processors of a device, cause the one or more processors to:

generate a displayable background area, wherein the displayable background area is selected from one of:

a beach background, a forest background, a pathway background, a bedroom background, and a bookstore background;

receive a request to generate an electronic character; receive an electronic communication that includes information about different features of the electronic character;

generate an electronic character that includes the different features, wherein the different features of the electronic character include:

facial expressions, facial features including a nose, eyes, and a mouth, and a particular electronically generated emotion;

display the electronic character;

generate an electronic light being;

display the electronic light being at the same time that the electronic character is being displayed, wherein:

the electronic character and the electronic light being are displayed within the displayable background area, the electronic character and the electronic light being, when displayed, in separate areas of the displayable background area, the electronic light being does not have any facial expressions or facial features, the electronic light being has a level of displayable light that is adjustable, wherein the adjustability of the displayable light is based on the particularly electronically generated emotion of the electronic character, and the electronic light being is based on electronic inputs;

display the electronic light being;

generate an action by the electronic light being;

change the level of displayable light based on the action of the electronic light being;

automatically contract the electronic light being size at the same time that the electronic light being generates an electronic audible communication, wherein the contracted size of the electronic light being and the electronic audible communication occur based on the changing the level of displayable light of the electronic light being; generate the same action by the electronic character;

automatically change the electronically generated emotion of the electronic character based on the action of the electronic light being; and, automatically change the displayable background area based on the generated emotion of the electronic character;

receive, after a time delay, another electronic communication that is then sent to another computing device associated with a therapist.

* * * * *